(12) United States Patent
Miyahara (10) Patent No.: US 7,571,889 B2
(45) Date of Patent: Aug. 11, 2009

(54) TUBE CLAMP (75) Inventor: Hideyasu Miyahara, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 414 days.

(21) Appl. No.: 11/661,026

(22) PCT Filed: Aug. 18, 2005

(86) PCT No.: PCT/JP2005/015082

§ 371 (c)(1),
(2), (4) Date: Feb. 23, 2007

(87) PCT Pub. No.: WO2006/022189

PCT Pub. Date: Mar. 2, 2006

(65) Prior Publication Data

US 2008/0029721 A1 Feb. 7, 2008

(30) Foreign Application Priority Data

Aug. 25, 2004 (JP) ............................. 2004-245496

(51) Int. Cl.
*F16K 7/04* (2006.01)

(52) U.S. Cl. .................. 251/6; 251/4; 604/34; 604/250
(58) Field of Classification Search ............ 251/6, 251/4; 604/34, 250, 251
See application file for complete search history.

(56) References Cited

U.S. PATENT DOCUMENTS 4,265,425 A    5/1981    Morin
(Continued)

FOREIGN PATENT DOCUMENTS

JP        55-72986        6/1980
(Continued)

OTHER PUBLICATIONS

International Search Report from the corresponding PCT/JP2005/015082, mailed Nov. 22, 2005.
(Continued)

*Primary Examiner*—John Rivell
*Assistant Examiner*—Andrew J Rost
(74) *Attorney, Agent, or Firm*—Hamre, Schumann, Mueller & Larson, P.C.

(57) ABSTRACT

A tube clamp includes a housing 1 that has an inner cavity 2 longitudinally passing through the housing 1 and an upper window 3, and a roller 4 that is mounted in the housing with its cylindrical surface positioned at the upper window and is movable longitudinally in the inner cavity. A pair of guide grooves 6 is formed along the upper window and guides a roller shaft 5. A distance between a bottom face 7 of the inner cavity and the guide grooves is smaller in a pinching region 7*b* than in an open region 7*a*. When the roller is positioned in the pinching region, a tube 11 is closed between the roller and the bottom face, and when the roller is positioned in the open region, the flow path in the tube is opened. The tube clamp further includes a slider 8 that is attached over the roller and is movable together with the roller in the inner cavity. The slider has slider shafts 9 that are provided on each side of the rear end of the slider and engaged with the guide grooves, and bearing notches 10 that are provided on the lower sides of the front end of the slider and fitted to the roller shaft for supporting the roller. The tube clamp can be operated easily with a light force and exert a sufficient force to close the tube.

6 Claims, 5 Drawing Sheets

U.S. PATENT DOCUMENTS

| | | | |
|---|---|---|---|
| 4,337,791 A * | 7/1982 | Tech et al. | 251/6 |
| 4,340,201 A * | 7/1982 | Becker, Jr. | 251/6 |
| RE31,584 E * | 5/1984 | Adelberg | 251/6 |
| 4,919,389 A * | 4/1990 | Hoekwater et al. | 251/6 |
| 5,830,195 A | 11/1998 | Peters et al. | |
| 6,415,960 B1 * | 7/2002 | Fink et al. | 222/175 |
| 6,536,739 B1 * | 3/2003 | Jensen | 251/6 |

FOREIGN PATENT DOCUMENTS

| | | |
|---|---|---|
| JP | 61-76169 | 4/1986 |
| JP | 7-39581 | 2/1995 |
| JP | 7-100207 | 4/1995 |
| JP | 9-508840 | 9/1997 |

OTHER PUBLICATIONS

Japanese Office Action, dated Oct. 28, 2008.

* cited by examiner

TUBE CLAMP

TECHNICAL FIELD

The present invention relates to a tube clamp for pinching a flexible tube to close the lumen of the tube or to control the cross sectional area of a flow path through the lumen of the tube.

BACKGROUND ART

For infusion or blood transfusion, a chemical solution or blood is transferred from an infusion bag or blood transfusion bag to a patient using a flexible tube. In peritoneal dialysis, e.g., a silicone rubber peritoneal catheter is inserted into the patient's abdominal cavity, and a dialyzate solution is introduced into and drained from the abdominal cavity through a transfer tube (extension tube) connected to the peritoneal catheter. The transfer tube is provided with a tube clamp that closes the tube so as to prevent leakage of the dialyzate solution stored in the abdominal cavity.

In a commonly used tube clamp, a roller that functions as a pressing member for closing a tube is mounted movably in a housing (see, e.g., JP 55(1980)-72986 A (Patent Document 1)). When the roller is moved by rotating it with a finger, a clearance between the roller and the base of the housing varies with changes in the position of the roller. This allows the tube to be compressed and released.

JP 7(1995)-100207 A (Patent Document 2) discloses a tube clamp that is similar in clamping action to that of Patent Document 1, but has been modified to facilitate the manipulation. The tube clamp of Patent Document 2 uses, instead of the roller, a movable pressing member combined with a control member in the form of a lever for moving the pressing member in a housing. The pressing member does not need to be operated directly with a finger, and the control member pivots about a point (fulcrum) of attachment to the housing. The control member is designed so that the path of a rotational movement of its end portion crosses the rear end of the pressing member. At the crossing position, the end portion of the control member abuts on the rear end of the pressing member and moves the pressing member in the direction of clamping the tube. The clamping operation by the control member rather than the pressing member itself can be performed easily and reliably with a smaller force.

Patent Document 1: JP 55(1980)-72986 A
Patent Document 2: JP 7(1995)-100207 A

DISCLOSURE OF INVENTION

Problem to be Solved by the Invention

When the roller is operated with a finger as disclosed in Patent Document 1, a considerable force is required to rotate and move the roller linearly. Therefore, it is difficult for the operator to perform a sensitive operation. The roller diameter should be made larger to reduce the manual force and improve the manipulability. On the other hand, a smaller diameter of the roller is advantageous in reliably closing the tube with small pressure. Accordingly, the structure of Patent Document 1 involves a structural contradiction that interferes with simultaneous improvements in the ease of manipulation and the reliability of a closing action.

The structure of Patent Document 2 may improve the manipulability. However, the pressing member is moved by abutment associated with the rotation of the control member. Therefore, the pressing member should be large enough to ensure a sufficient amount of movement. In view of this, the structure is unsuitable for reducing the size of the pressing member and achieving a reliable closing action with small pressure. Moreover, since the pressing member does not rotate, when the pressing member is moved to close the tube, it slides against the tube. This may increase damage to the tube due to friction.

In both structures of Patent Documents 1 and 2, the housing is divided into two parts for mounting the roller or the pressing member and the control member in the housing. That is, the roller or the pressing member and the control member are sandwiched between the two parts of the housing, and subsequently the two parts are joined with ultrasonic welding or an adhesive. In this manner, it is possible not only to avoid the members such as a roller being detached when mounted in the housing, but also to prevent the mounted members from slipping off during operation. Thus, the dimensional accuracy of the housing and the members such as a roller must be controlled strictly.

When the housing is assembled by techniques such as ultrasonic welding or adhesive bonding, an internal stress is likely to be generated at the joint due to distortion, and the stress is always applied to the members. This causes considerable damage to the members that have been subjected to the stress. Moreover, such damage becomes apparent gradually over long periods of use, and finally may lead to a fracture. When strict control of the dimensional accuracy is required, there is a possibility that the intended function will not be performed because of a change in dimension caused by the wear of the components or the like.

With the foregoing in mind, it is an object of the present invention to provide a tube clamp that can be operated easily with a light force, and also can exert a sufficient force to close a tube.

It is another object of the present invention to provide a tube clamp that has a simple structure for holding a clamp member that includes a roller for pressing a tube in a housing, and can be assembled without including a manufacturing process that may cause a fracture over long periods of use.

Means for Solving Problem

A tube clamp of the present invention includes a housing that has an inner cavity longitudinally passing through the housing, the inner cavity being open upward to form an upper window, and a roller that is mounted in the inner cavity of the housing with its cylindrical surface positioned at the upper window and is movable longitudinally in the inner cavity. Guide grooves are formed in both side walls of the inner cavity, extend longitudinally along the upper window, and guide a roller shaft of the roller. A distance between the bottom face of the inner cavity and the guide grooves is smaller in a pinching region provided in either the front portion or the rear portion of the inner cavity than in an open region provided in the other portion. When the roller is positioned in the pinching region, a tube inserted through the inner cavity is closed by being pressed between the roller and the bottom face of the inner cavity, and when the roller is positioned in the open region, the tube is opened.

To solve the above problems, the tube clamp of the present invention further includes a slider that is attached over the roller so that the top surface of the slider is exposed from the upper window and is movable together with the roller in the inner cavity of the housing. The slider has a pair of slider shafts and bearing notches. The pair of slider shafts is provided on each side of the rear end of the slider and engaged with the guide grooves. The bearing notches are provided on the lower sides of the front end of the slider and fitted to the roller shaft for supporting the roller. The slider shafts and the roller shaft are guided together by the guide grooves.

EFFECTS OF THE INVENTION

With the above configuration, the roller is rotated via linear movement of the slider. Therefore, even if the roller has a small diameter, a clamping operation can be performed easily with a light force. Moreover, the roller can exert a sufficient force to close the tube. Thus, it is possible to improve the ease of manipulation and the reliability of a closing action simultaneously.

DESCRIPTION OF REFERENCE NUMERALS

1 Housing
2 Inner cavity
3 Upper window
4 Roller
5 Roller shaft
6 Guide groove
6a Lower stepped portion
7 Bottom face
7a Open region
7b Pinching region
7c Intermediate region
8 Slider
9 Slider shaft
10 Bearing notch
11 Tube
12 Notched groove
13 Upper wall
14 Front edge
15 Latch
16 Latch projection
17 Engagement groove

BEST MODE FOR CARRYING OUT THE INVENTION

In the tube clamp of the present invention, the pinching region may be located at the rear portion of the inner cavity.
Preferably, a pair of notched grooves is formed in the side edges of the front end of the upper window and communicates with the pair of guide grooves from above, respectively, and the slider can be inserted into the inner cavity through the upper window by sliding the slider shafts backwards in the guide grooves via the notched grooves. At the front end opening of the inner cavity, the upper wall of the inner cavity and a lower stepped portion of each of the guide grooves are spaced so that the roller can be inserted into the inner cavity through the front end opening while the roller shaft is positioned in the guide grooves. The roller and the slider are combined into one body by fitting the roller shaft into the bearing notches, and when the slider is positioned at the front end of the upper window, the front end of the slider is restrained from moving further forward by the front edge of the upper window.

The width of an open end of each of the bearing notches is smaller than the diameter of the roller shaft, and the open ends of the bearing notches are enlarged by elastic deformation as the roller shaft is pressed into the bearing notches, so that the roller shaft can be fitted into the bearing notches.

The tube clamp further may include a latch provided at the rear end of the slider and a latch projection formed on the inner surface of the housing in the vicinity of the rear end of the upper window. When the roller is positioned in the pinching region, the latch and the latch projection may be engaged with each other to prevent the slider from moving forward.

Alternatively, the tube clamp further may include engagement grooves formed in the inner wall of the housing above the guide grooves so as to reach stepped portions of the guide grooves. When the roller is positioned in the pinching region, the roller shaft can be engaged with the engagement grooves.

Hereinafter, embodiments of the present invention will be described in detail with reference to the drawings.

Embodiment 1

Figure 1:
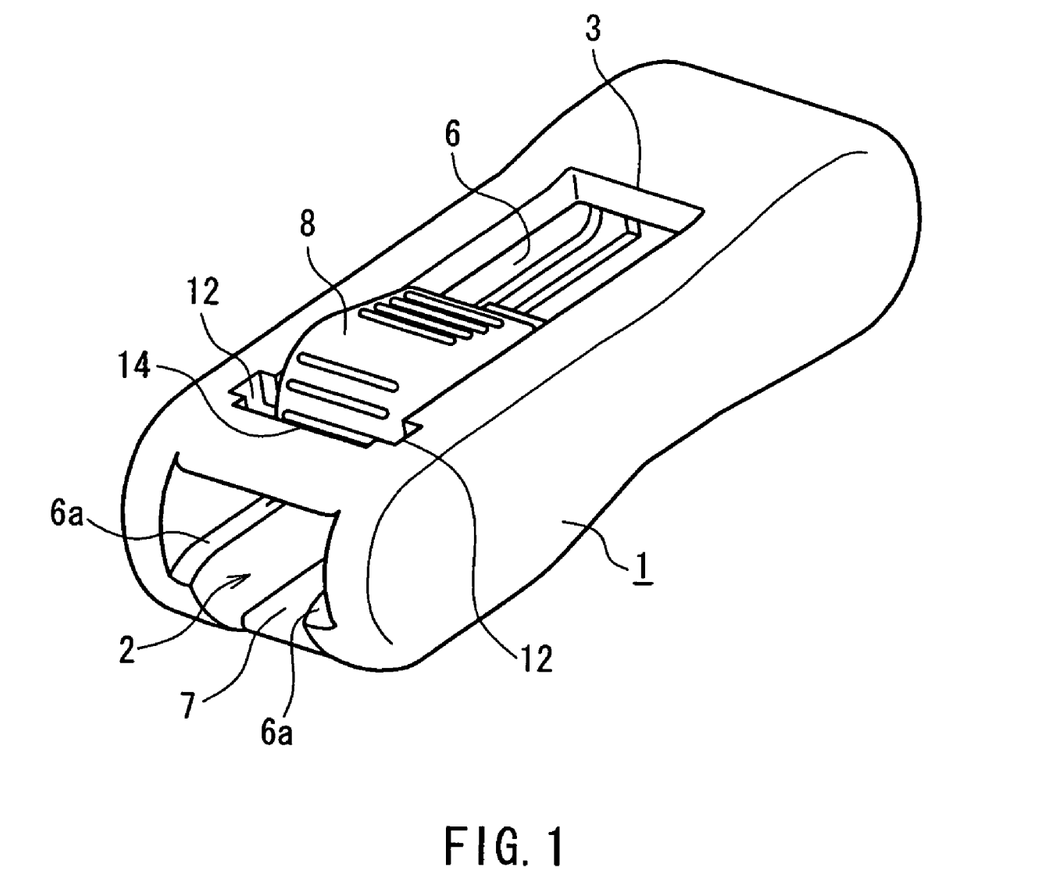
FIG. 1 is a perspective view showing a tube clamp of Embodiment 1 of the present invention.
Figure 2:
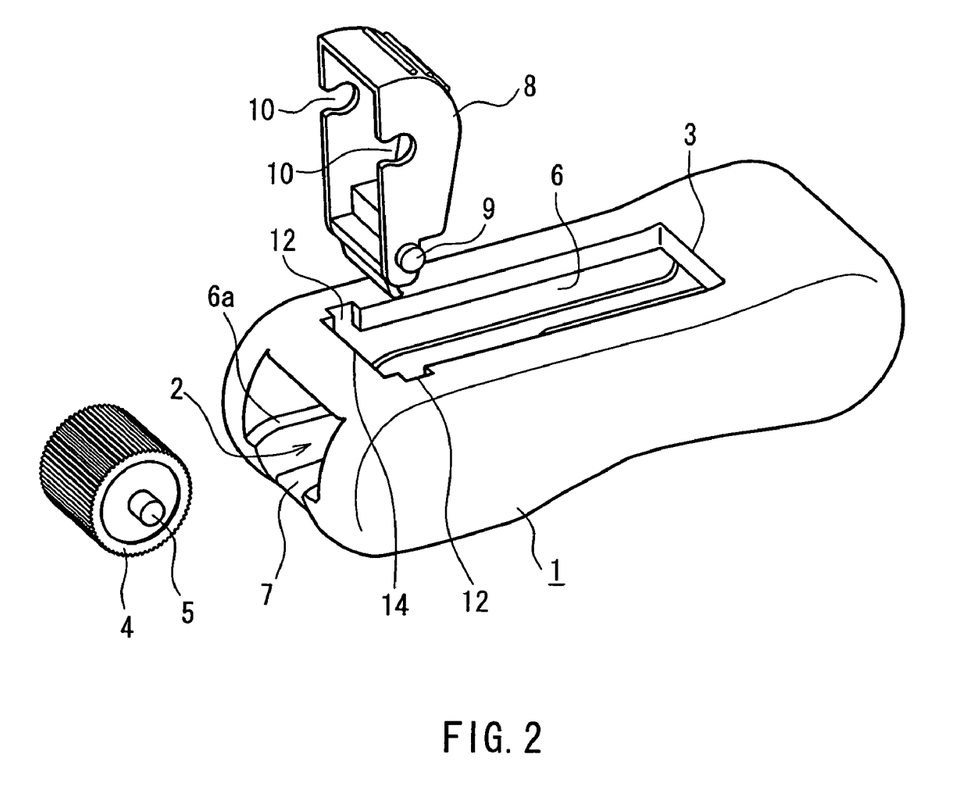
FIG. 2 is an exploded perspective view of the tube clamp.
Figure 3:
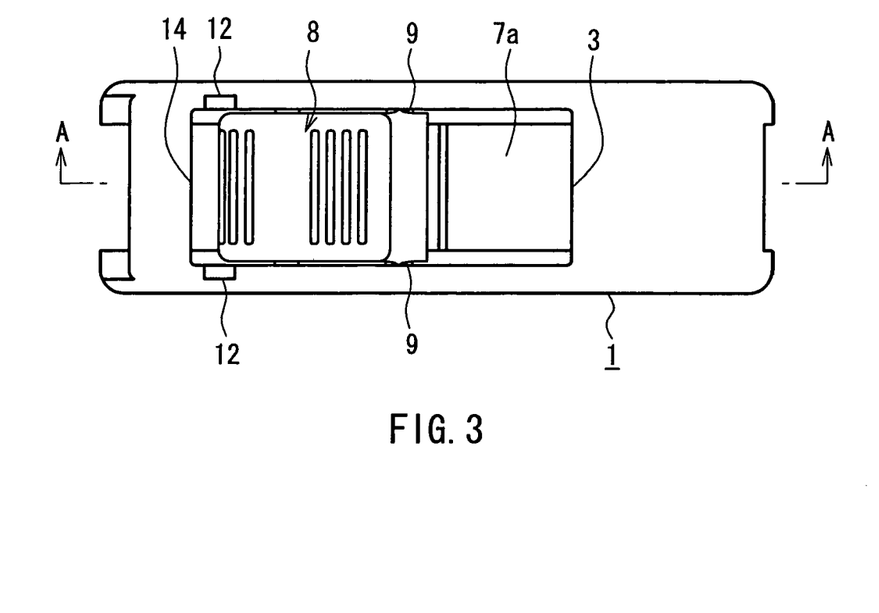
FIG. 3 is a plan view of the tube clamp.
Figure 4:
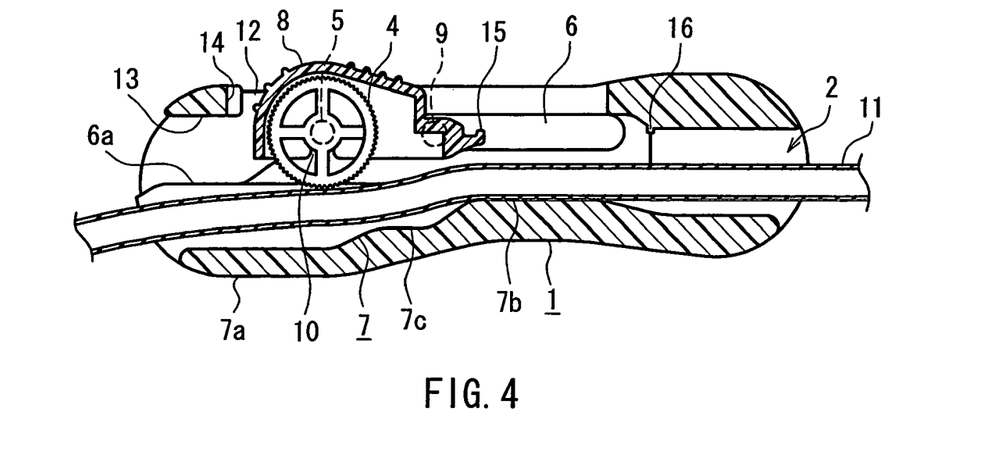
FIG. 4 is a cross-sectional view taken along the line A-A in FIG. 3.

FIG. 1 is a perspective view showing a tube clamp of Embodiment 1 of the present invention. FIG. 2 is an exploded perspective view of the tube clamp. FIG. 3 is a plan view of the tube clamp. FIG. 4 is a cross-sectional view taken along the line A-A in FIG. 3.

A housing 1 has an inner cavity 2 longitudinally passing though the housing 1, and the inner cavity 2 is open upward to form an upper window 3. A roller 4 is mounted in the inner cavity 2 of the housing 1 with its cylindrical surface positioned at the upper window 3. The roller 4 is movable longitudinally in the inner cavity 2. A pair of guide grooves 6 is formed in both side walls of the inner cavity 2 and extends longitudinally along the upper window 3. The roller 4 is moved in the inner cavity 2 while a roller shaft 5 is guided by the guide grooves 6. A bottom face 7 of the inner cavity 2 forms an open region 7a in the front portion of the inner cavity 2, where the distance between the bottom face 7 and the guide grooves 6 is sufficiently large. The bottom face 7 forms a pinching region 7b in the rear portion of the inner cavity 2, where the distance between the bottom face 7 and the guide grooves 6 is smaller than that in the open region 7a. The bottom face 7 forms an intermediate region 7c provided between the open region 7a and the pinching region 7b, where the distance ranges from that in the open region 7a to that in the pinching region 7b. The distance may be changed gradually in the intermediate region 7c.

A slider 8 is attached so as to cover the upper portion of the roller 4. The top surface of the slider 8 is exposed from the upper window 3 of the housing 1. The slider 8 is movable together with the roller 4 in the inner cavity 2, thus constituting a clamp member. The slider 8 has a pair of slider shafts 9 and bearing notches 10. The pair of slider shafts 9 is provided on each side of the rear end of the slider 8 and engaged with the guide grooves 6. The bearing notches 10 are provided on the lower sides of the front end of the slider 8 and fitted to the roller shaft 5 for supporting the roller 4. Under these conditions, the slider shafts 9 and the roller shaft 5 are guided together by the guide grooves 6. All of the housing 1, the roller 4, and the slider 8 may be, e.g., molded plastics.

Figure 5:
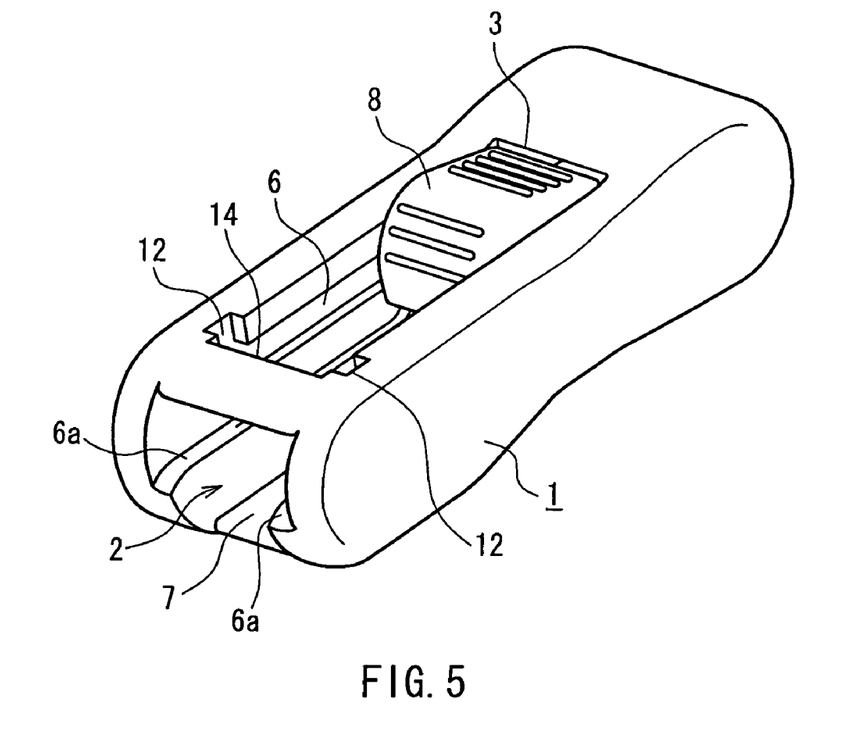
FIG. 5 is a perspective view of the tube clamp in which a roller and a slider are positioned in a pinching region.
Figure 6:
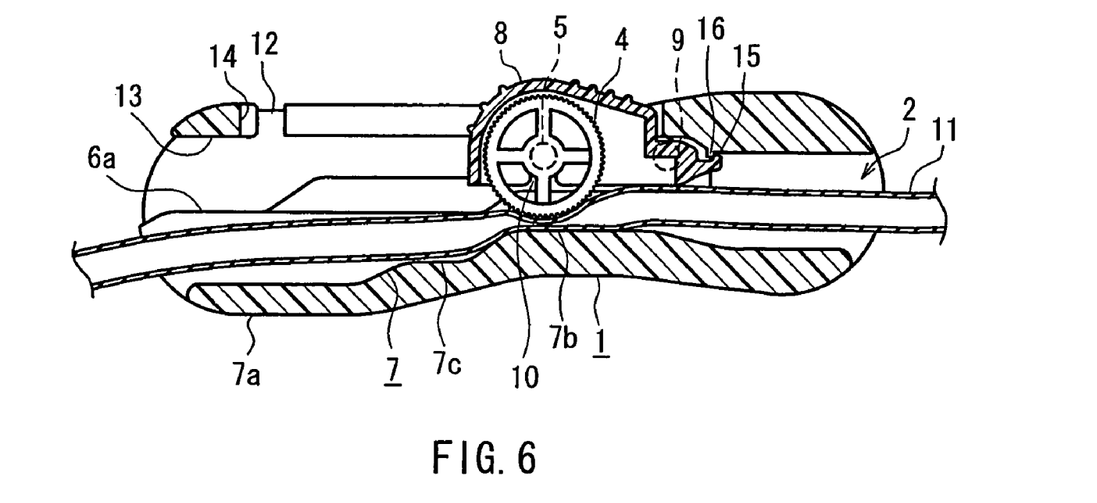
FIG. 6 is a cross-sectional view of the tube clamp in FIG. 5, taken along the line A-A in FIG. 3.

As shown in FIG. 4, a flexible tube 11 is inserted through the inner cavity 2, and then the top surface of the slider 8 is pushed with a finger so that the roller 4 combined with the slider 8 is moved back and forth, thereby adjusting the clamped state of the tube 11. For example, when the roller 4 is positioned in the open region 7a of the inner cavity 2, as shown in FIG. 4, the lumen of the tube 11 is opened and fully functions as a flow path. In this position, the bottom face 7 of the inner cavity 2 has a sufficient distance from the guide grooves 6. Therefore, an adequate space is maintained between the circumferential surface of the roller 4 and the bottom face 7 of the inner cavity 2, and no force of compression is exerted on the tube 11. In contrast, when the roller 4 is positioned in the pinching region 7b, as shown in FIGS. 5 and 6, the tube 11 is pressed between the roller 4 and the bottom face 7, so that the lumen of the tube 11 is closed. When the roller 4 is positioned in the intermediate region 7c, the flow rate can be adjusted by changing the cross section of the lumen of the tube 11. The shape of the bottom face 7 in the intermediate region 7c, i.e., a change in distance between the bottom face 7 and the guide grooves 6 may be determined appropriately to make the manipulation suitable for the flow rate adjustment.

With this configuration, the roller 4 is rotated via linear movement of the slider 8. Therefore, even if the roller 4 has a small diameter, a clamping operation can be performed easily with a light force. Moreover, the roller 4 can exert a sufficient force to close the tube 11. Thus, it is possible to improve the ease of manipulation and the reliability of a closing action simultaneously.

The tube clamp further has a modified structure that allows the roller 4 and the slider 8 to be combined into one body and mounted in the housing 1. A pair of notched grooves 12 is formed in the side edges of the front end of the upper window 3 and communicates with the pair of guide grooves 6 from above, respectively. The slider 8 in the state as shown in FIG. 2 is inserted into the inner cavity 2 through the upper window 3 while the slider shafts 9 go through the notched grooves 12. In other words, the slider 8 is inserted into the inner cavity 2 through the upper window 3 by sliding the slider shafts 9 backwards in the guide grooves 6 via the notched grooves 12.

At the front end opening of the inner cavity 2, an upper wall 13 of the inner cavity 2 and a lower stepped portion 6a of each of the guide grooves 6 are spaced so that the roller 4 can be inserted into the inner cavity 2 through the front end opening. Therefore, the roller 4 in the state as shown in FIG. 2 is inserted into the inner cavity 2 while the roller shaft 5 is positioned in the guide grooves 6.

The slider 8 and the roller 4 are mounted in the housing 1 in the above manner, and the roller shaft 5 is fitted into the bearing notches 10, thereby combining the roller 4 and the slider 8 into one body. As a result of the combination of the roller 4 and the slider 8, when the slider 8 is positioned at the front end of the upper window 3, as shown in FIGS. 3 and 4, the front end of the slider 8 comes into contact with a front edge 14 of the upper window 3 and thus is restrained from moving further forward. Moreover, since the slider shafts 9 and the roller shaft 5 are engaged with the guide grooves 6, the slider 8 does not detach upwardly from the upper window 3. Accordingly, when the roller 4 and the slider 8 are combined into one body, the state of the combined body mounted in the housing 1 is retained by the engagement of the slider shafts 9 and the roller shaft 5 with the guide grooves 6 and by the restriction on movement of the front end of the slider 8 due to the front edge 14 of the upper window 3.

The roller 4 and the slider 8 remain combined by fitting the roller shaft 5 into the bearing notches 10. The width of an open end of each of the bearing notches 10 is smaller than the diameter of the roller shaft 5. Therefore, when the roller shaft 5 is fitted into the bearing notches 10, the open ends of the bearing notches 10 are enlarged by elastic deformation as the roller shaft 5 is pressed into the bearing notches 10. Thus, once the roller shaft 5 and the bearing notches 10 are fitted together, the roller shaft 5 will not slip off the bearing notches 10 unless a strong force is applied to the roller shaft 5 that may cause elastic deformation in the open ends of the bearing notches 10.

As described above, the roller 4 and the slider 8 are inserted separately into the housing 1 and then combined into one body, so that mounting of the clamp member in the housing 1 is completed. In this state, since the combined body of the roller 4 and the slider 8 has outer dimensions that cannot be removed from the housing 1, the mounted state of the clamp member is ensured. The structure for holding the tube 11 and the clamp member composed of the roller 4 and the slider 8 in the housing 1 is simple and its holding action is reliable. Moreover, the tube clamp with this structure does not require ultrasonic welding or adhesive bonding that may lead to a fracture over long periods of use, and exhibits high durability because no stress, other than that caused by the tube, is generated in each part after assembly.

The tube clamp further includes a lock mechanism for preventing movement of the slider 8 to keep the position of the roller 4 when it is positioned in the pinching region 7b. As shown in FIG. 4, the lock mechanism includes a latch 15 provided at the rear end of the slider 8 and a latch projection 16 formed on the inner surface of the housing 1 in the vicinity of the rear end of the upper window 3. As shown in FIG. 6, when the roller 4 is positioned in the pinching region 7b, the latch 15 and the latch projection 16 are engaged with each other to prevent the slider 8 from moving forward. This state may be unlocked by pressing the slider 8 down against the elastic force of the tube 11 so that the latch 15 and the latch projection 16 are disengaged.

Moreover, the engagement of the latch 15 and the latch projection 16 can have an effect of confirming the completion of a closing operation. During the closing operation of the clamp, when the slider 8 is moved and the latch 15 is engaged with the latch projection 16, the lock mechanism works and makes a "click" sound along with the engagement. At the same time, the operator's fingers also feel the click. Therefore, the operator can recognize the "completion of the closing operation" by an auditory signal and/or tactile signal. A series of these actions resulting from the engagement of the latch 15 and the latch projection 16 can improve the manipulation totally.

Embodiment 2

Figure 7:
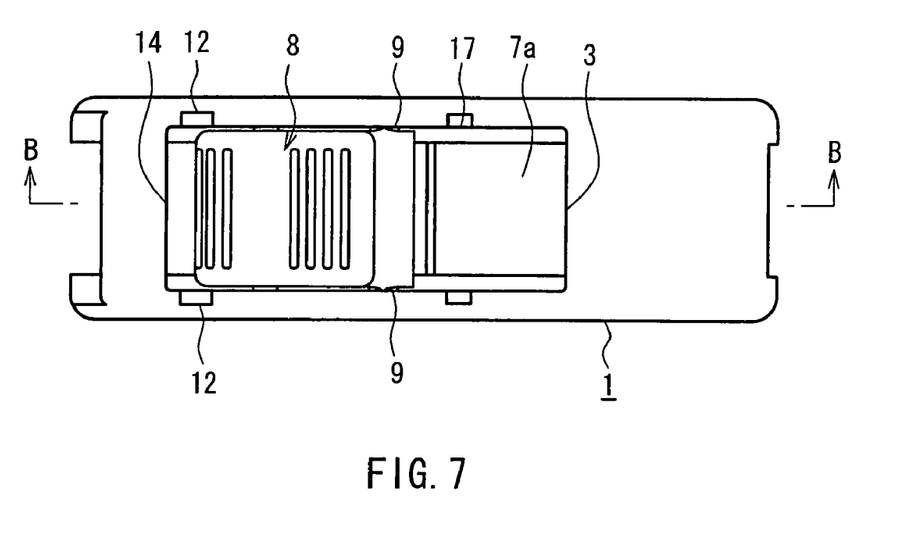
FIG. 7 is a plan view showing a tube clamp of Embodiment 2 of the present invention.
Figure 8:
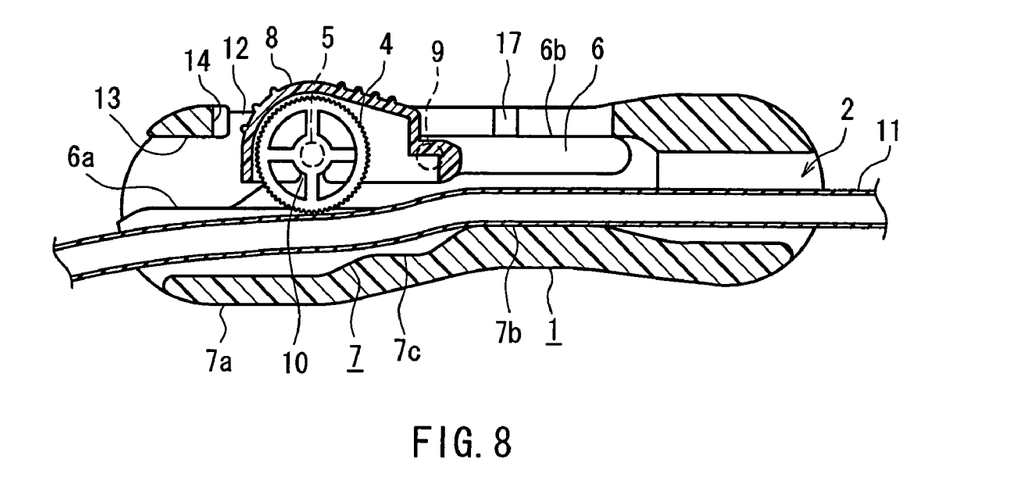
FIG. 8 is a cross-sectional view taken along the line B-B in FIG. 7.

FIG. 7 is a plan view showing a tube clamp of Embodiment 2 of the present invention. FIG. 8 is a cross-sectional view taken along the line B-B in FIG. 7.

This embodiment is the same as Embodiment 1 in basic configuration and includes a roller stopper mechanism for stopping movement of the roller 4 and keeping the position of the roller 4 in the pinching region 7b. The roller stopper mechanism may be used instead of the lock mechanism by the engagement of the latch 15 and the latch projection 16 in Embodiment 1.

In FIGS. 7 and 8, engagement grooves 17 constitute the roller stopper mechanism. The engagement grooves 17 are formed in the inner walls of the housing 1 above the guide grooves 6 so as to reach upper stepped portions 6b of the guide grooves 6. The position of the engagement grooves 17 is determined so that the roller shaft 5 can be engaged with the engagement grooves 17 when the roller 4 is positioned in the pinching region 7b. The breadth (width) of the engagement grooves 17 is smaller than the diameter of the roller shaft 5, but is set such that part of the roller shaft 5 is fitted into the engagement grooves 17.

The roller shaft 5 is slid in the guide grooves 6, and the upper portion of the roller shaft 5 is fitted into the engagement grooves 17 when the roller 4 is positioned in the pinching region 7b. Therefore, a force is applied against the movement of the roller shaft 5 in the direction of the guide grooves 6 to stop the roller 4 from moving. While the roller 4 presses the tube 11 in the pinching region 7b, it is pushed upward by repulsion from the tube 11. This exerts a force that causes the roller shaft 5 to be fitted into the engagement grooves 17. Thus, the engagement grooves 17 simply can serve as the roller stopper mechanism at the predetermined position. Moreover, the operator clearly feels the fit between the roller shaft 5 and the engagement grooves 17 when they are engaged, resulting in good manipulability. For disengagement, the manual force applied to the roller 4 via the slider 8 in its direction directly acts as a force that separates the roller shaft 5 from the engagement grooves 17. Therefore, the operation is easy.

In view of the formability of the housing 1, it is desirable that the engagement grooves 17 pass through the housing 1 in the direction perpendicular to the guide grooves 6, as shown in the drawings. However, in relation to other conditions, the engagement groove 17 may be a groove that does not pass completely through the housing 1 and has an opening only on the lower side, or may be in the form of a shallow recess instead of a groove.

Instead of the above configurations, e.g., a mechanism for fastening the slider shafts 9 also may be provided to keep the position of the roller 4 in the pinching region 7b. Specifically, an engagement hole is formed in the wall of each of the guide grooves 6 at the position opposite to the end of the slider shaft 9. When the roller 4 is positioned in the pinching region 7b, the ends of the slider shafts 9 are fitted into the engagement holes, respectively. For this purpose, it is desirable that the position, shape, and size of the slider shafts 9 of the slider 8 are determined so that the ends of the slider shafts 9 are pressed against the walls of the guide grooves 6.

As described above, the tube clamp in each of the embodiments of the present invention has a clamping mechanism by combining the roller 4 and the slider 8. The clamping operation is performed only by linear movement of the slider 8, and the roller 4 needs not to be operated with a finger. Therefore, even if the roller has a small diameter, which is suitable for a reliable clamping action, the effect on the manipulation is small.

INDUSTRIAL APPLICABILITY

A tube clamp of the present invention can be operated easily with a light force, and also can exert a sufficient force to close a tube. Accordingly, the tube clamp is useful as a member for clamping a tube used for infusion or blood transfusion.

The invention claimed is:
1. A tube clamp comprising:
a housing that has an inner cavity longitudinally passing through the housing, the inner cavity being open upward to form an upper window; and
a roller that is mounted in the inner cavity of the housing with its cylindrical surface positioned at the upper window and is movable longitudinally in the inner cavity,
wherein guide grooves are formed in both side walls of the inner cavity, extend longitudinally along the upper window, and guide a roller shaft of the roller,
wherein a distance between a bottom face of the inner cavity and the guide grooves is smaller in a pinching region provided in either a front portion or a rear portion of the inner cavity than in an open region provided in the other portion, and
wherein when the roller is positioned in the pinching region, a tube inserted through the inner cavity is closed by being pressed between the roller and the bottom face of the inner cavity, and when the roller is positioned in the open region, the tube is opened,
the tube clamp further comprising a slider that is attached over the roller so that a top surface of the slider is exposed from the upper window and is movable together with the roller in the inner cavity of the housing,
wherein the slider has a pair of slider shafts and bearing notches, the pair of slider shafts is provided on each side of a rear end of the slider and engaged with the guide grooves, the bearing notches are provided on lower sides of a front end of the slider and fitted to the roller shaft for supporting the roller, and the slider shafts and the roller shaft are guided together by the guide grooves.

2. The tube clamp according to claim 1, wherein the pinching region is located at the rear portion of the inner cavity.

3. The tube clamp according to claim 1, wherein a pair of notched grooves is formed in side edges of a front end of the upper window and communicates with the pair of guide grooves from above, respectively, and the slider can be inserted into the inner cavity through the upper window by sliding the slider shafts backwards in the guide grooves via the notched grooves,
wherein at a front end opening of the inner cavity, an upper wall of the inner cavity and a lower stepped portion of each of the guide grooves are spaced so that the roller can be inserted into the inner cavity through the front end opening while the roller shaft is positioned in the guide grooves, and
wherein the roller and the slider are combined into one body by fitting the roller shaft into the bearing notches, and when the slider is positioned at the front end of the upper window, the front end of the slider is restrained from moving further forward by a front edge of the upper window.

4. The tube clamp according to claim 3, wherein a width of an open end of each of the bearing notches is smaller than a diameter of the roller shaft, and the open ends of the bearing notches are enlarged by elastic deformation as the roller shaft is pressed into the bearing notches, so that the roller shaft is fitted into the bearing notches.

5. The tube clamp according to claim 1, further comprising a latch provided at the rear end of the slider and a latch projection formed on an inner surface of the housing in the vicinity of a rear end of the upper window,
wherein when the roller is positioned in the pinching region, the latch and the latch projection are engaged with each other to prevent the slider from moving forward.

6. The tube clamp according to claim 1, further comprising engagement grooves formed in an inner wall of the housing above the guide grooves so as to reach stepped portions of the guide grooves,
wherein when the roller is positioned in the pinching region, the roller shaft can be engaged with the engagement grooves.

* * * * *